(12) United States Patent
Jackson

(10) Patent No.: US 11,547,831 B1
(45) Date of Patent: Jan. 10, 2023

(54) VIRTUAL REALITY AUGMENTED MASSAGE THERAPY SYSTEM AND METHOD

(71) Applicant: Micah D Jackson, Windsor Hills, CA (US)

(72) Inventor: Micah D Jackson, Windsor Hills, CA (US)

( * ) Notice: Subject to any disclaimer, the term of this patent is extended or adjusted under 35 U.S.C. 154(b) by 912 days.

(21) Appl. No.: 16/410,129

(22) Filed: May 13, 2019

Related U.S. Application Data

(63) Continuation of application No. 62/828,343, filed on Apr. 2, 2019.

(51) Int. Cl.
| | |
|---|---|
| *A61M 21/02* | (2006.01) |
| *G06F 3/16* | (2006.01) |
| *G09G 5/00* | (2006.01) |
| *A61F 7/00* | (2006.01) |
| *A61H 7/00* | (2006.01) |
| *G06F 3/01* | (2006.01) |
| *A61M 21/00* | (2006.01) |

(52) U.S. Cl.
CPC ............... *A61M 21/02* (2013.01); *A61F 7/00* (2013.01); *A61H 7/00* (2013.01); *G06F 3/011* (2013.01); *G06F 3/165* (2013.01); *G09G 5/003* (2013.01); *A61F 2007/0088* (2013.01); *A61H 2201/0149* (2013.01); *A61H 2201/102* (2013.01); *A61M 2021/005* (2013.01); *A61M 2021/0016* (2013.01); *A61M 2021/0022* (2013.01); *A61M 2021/0027* (2013.01); *A61M 2021/0066* (2013.01); *A61M 2205/07* (2013.01)

(58) Field of Classification Search
CPC .................. A61M 21/00; A61M 21/02; A61M 2021/0005; A61F 7/00; A61H 7/00; G06F 3/011; G06F 3/165; G09G 5/003
See application file for complete search history.

(56) References Cited

U.S. PATENT DOCUMENTS

| | | | | |
|---|---|---|---|---|
| 3,826,250 | A * | 7/1974 | Adams | A61M 21/0094 601/16 |
| 4,893,615 | A * | 1/1990 | Khabirova | A61M 21/0094 601/16 |
| 5,266,070 | A * | 11/1993 | Hagiwara | A61M 21/00 600/27 |
| 6,702,767 | B1 * | 3/2004 | Douglas | A61M 21/0094 601/16 |
| 2018/0250190 | A1 * | 9/2018 | Masuda | G06F 3/011 |
| 2022/0054347 | A1 * | 2/2022 | Tan | G10L 15/22 |

* cited by examiner

*Primary Examiner* — John P Lacyk
(74) *Attorney, Agent, or Firm* — Plager Schack LLP; Mark H. Plager; Stephen Hallberg

(57) ABSTRACT

A virtual reality augmented massage therapy system and method is disclosed. Using this system taps into all of the key senses that people use to evaluate their surroundings, which in turn helps them to relax and feel comfortable. Simply stated, the more stimulus inputs a person's brain receives to determine its presence in an environment, the more immersed the person will become in the generated environment.

10 Claims, 3 Drawing Sheets

VIRTUAL REALITY AUGMENTED MASSAGE THERAPY SYSTEM AND METHOD

CLAIM OF BENEFIT TO PRIOR APPLICATION

This application claims benefit to U.S. Provisional Patent Application 62/828,343, entitled "A virtual reality augmented massage therapy system and method," filed Apr. 2, 2019. The U.S. Provisional Patent Application 62/828,343 is incorporated herein by reference.

BACKGROUND

Embodiments of the invention described in this specification relate generally to virtual reality (VR) systems, and more particularly, to a virtual reality augmented massage therapy system and a method for providing virtual reality augmented massage therapy.

Many people suffer from anxiety, panic attacks and depression which in many cases are influenced by or directly attributed to their daily routines and responsibilities. Having a way to regularly alter ones mental state through practical, holistic means, has proven to be an effective way to battle some of these physiological disorders.

Other methods of using VR to address anxiety and stress typically focus only on an audio and visual experiences which use a head-mounted display and some form of stand-alone or integrated computer. These types of singular VR experiences don't sync up with external devices or stimulate sensations like smell, temperature and touch. When relying on just an audio/visual VR experience, the sense of immersion is very limited.

Therefore, what is needed is a way to tap into all of the key senses that people use to evaluate their surroundings, which in turn helps them to relax and feel comfortable. Simply stated, the more sensory inputs a person's brain receives to determine its presence in an environment, the more immersed the person will become in the generated environment.

BRIEF DESCRIPTION

A novel virtual reality augmented massage therapy system and a novel method for providing virtual reality augmented massage therapy are disclosed. The virtual reality augmented massage therapy system and the method for providing virtual reality augmented massage therapy work on multiple sensory levels to help a user evaluate their surroundings in order help the user relax and feel comfortable during massage therapy. In some embodiments, the virtual reality augmented massage therapy system includes an automated massage chair, a virtual reality computing device, a virtual reality headset, an aromatherapy diffuser, heating lamps, and fans.

In some embodiments, the method for providing virtual reality augmented massage therapy includes a plurality of steps to engage multiple senses of a user to help the user evaluate their surroundings in order to relax and feel comfortable during massage therapy. In some embodiments, the plurality of steps of the method for providing virtual reality augmented massage therapy include (i) seating a user in an automated massage chair, (ii) placing a virtual reality headset onto the user to cover the user's eyes and ears, (iii) starting VR playback on the virtual reality headset by one of starting a virtual reality program on a virtual reality computing device that is communicably connected to the virtual reality headset and starting a VR content generator that is communicably connected to the virtual reality headset, (iv) initiating a massage program of a particular time duration by selection of a pre-programmed massage routine on the automated massage chair, (v) triggering a plurality of sensory devices comprising a fragrance diffuser, ceramic heat lamps, and fans, (vi) fading out the VR playback at the end of the particular time duration, and (vii) concluding the massage program by the automated massage chair.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
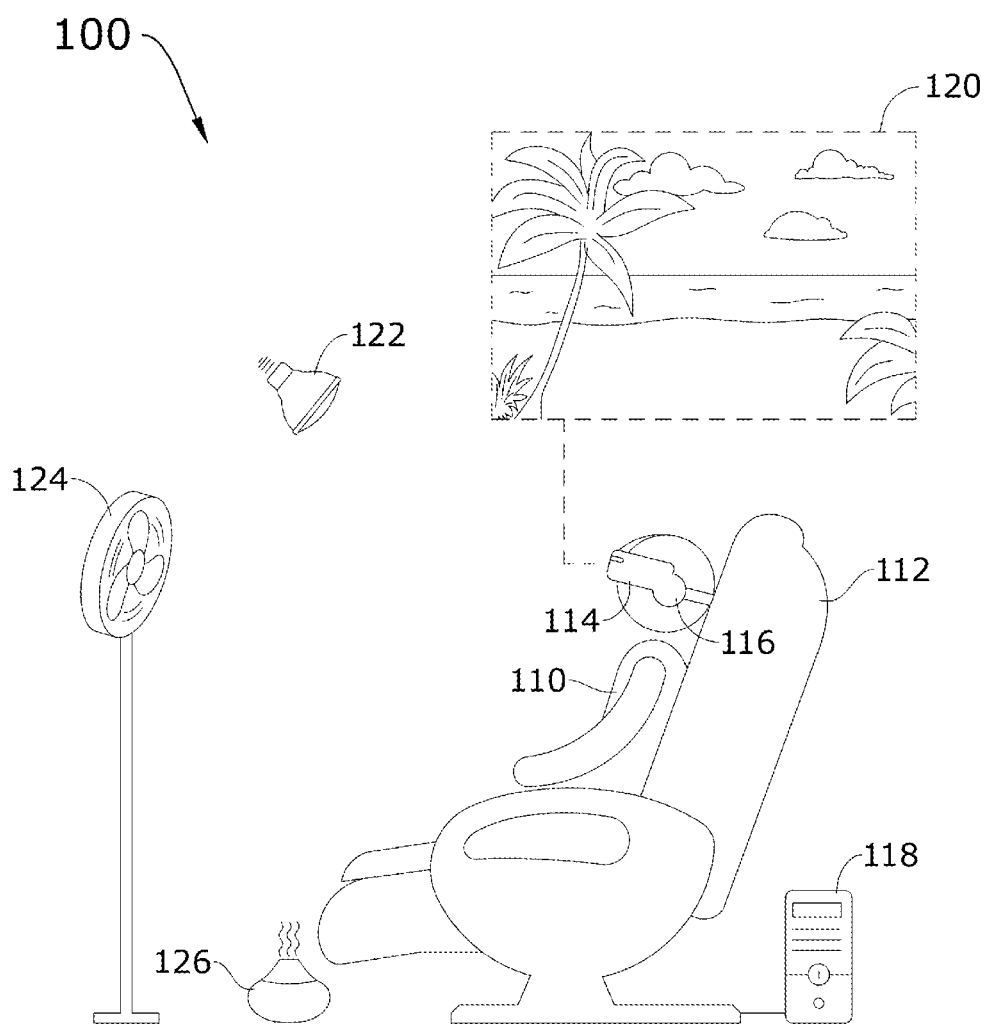
FIG. 1 conceptually illustrates a virtual reality augmented massage therapy system in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel virtual reality augmented massage therapy system and a novel method for providing virtual reality augmented massage therapy that works on multiple sensory levels to help a user evaluate their surroundings in order help the user relax and feel comfortable during massage therapy. In some embodiments, the virtual reality augmented massage therapy system includes an automated massage chair, a virtual reality computing device, a virtual reality headset, an aromatherapy diffuser, heating lamps, and fans.

As stated above, many people suffer from anxiety, panic attacks and depression which in many cases are influenced by or directly attributed to their daily routines and responsibilities. Having a way to regularly alter ones mental state through practical, holistic means, has proven to be an effective way to battle some of these physiological disorders. Embodiments of the virtual reality augmented massage therapy system and method for providing virtual reality augmented massage therapy described in this specification solve such problems by combining virtual reality environments with automated massage programs and individual sensory components creates a system by which a person's mood can be altered as they experience immersive relaxation through sight, sound, touch and smell.

Embodiments of the virtual reality augmented massage therapy system and method for providing virtual reality augmented massage therapy described in this specification differ from and improve upon currently existing conventional VR systems and conventional massage therapy delivery. In particular, some embodiments differ from conventional virtual reality (VR) systems which, to date, have been used to treat many physiological and psychological disorders; however the practice has largely focused solely on audio and visual immersion through a single head-mounted display (HMD). This proposed method pairs specifically designed VR experiences to programmed automated massages, curated fragrances and automated sensory controls that work together to create a heightened sense of immersion which has not been done before.

In addition, some embodiments of the virtual reality augmented massage therapy system and method for providing virtual reality augmented massage therapy improve upon the currently existing conventional VR systems, which have been used to treat many physiological and psychological disorders, but which have otherwise been lacking. Specifically, the conventional VR practice has largely focused solely on audio and visual immersion through a single head-mounted display (HMD). In contrast, the virtual reality augmented massage therapy system and method for providing virtual reality augmented massage therapy pairs specifically designed VR experiences to programmed automated massages, curated fragrances, and automated sensory controls that work together to create a heightened sense of immersion which has not been done before. This is especially helpful because, as humans, we rely on multiple senses to determine whether or not our environment is safe and pleasing. And while many factors come into play in making a full, personal determination, such as personal preferences and experiences, several common factors are more or less universally involved for all humans, including sight, sound, smell, and touch (with exceptions for humans who lack one or another of those senses) to evaluate their 'real-world' surroundings. Thus, by combining multiple of these common human "felt" sensations or experiences, the virtual reality augmented massage therapy system and method for providing virtual reality augmented massage therapy described in this specification improves upon those existing conventional VR systems, which normally operate by effectively limiting which senses are stimulated at any given time.

Furthermore, using the virtual reality augmented massage therapy system and method for providing virtual reality augmented massage therapy of the present disclosure helps a user to relax and feel comfortable by its immersive capabilities, which are premised on tapping into all of the key senses that people use to evaluate their surroundings. Simply stated, the more sensory inputs a person's brain receives to determine its presence in an environment, the more immersed the person will become in the generated environment. This immersive "felt sense" or "felt experience" lends authenticity to the generated environment at a sensory level, even when the user is logically aware of the imitative quality of the generated surroundings.

The virtual reality augmented massage therapy system of the present disclosure may be comprised of the following elements. This list of possible constituent elements is intended to be exemplary only and it is not intended that this list be used to limit the virtual reality augmented massage therapy system of the present application to just these elements. Persons having ordinary skill in the art relevant to the present disclosure may understand there to be equivalent elements that may be substituted within the present disclosure without changing the essential function or operation of the virtual reality augmented massage therapy system.

1. Automated Massage Chair
2. Computer or VR Content Generator
3. Virtual Reality Headset
4. Aromatherapy Diffuser
5. Ceramic Heat Lamps
6. Fans By way of example, FIG. 1 conceptually illustrates a virtual reality augmented massage therapy system 100. As shown in this example, the virtual reality augmented massage therapy system 100 includes a user 110, an automated massage chair 112, a virtual reality headset 114, headphones 116, a computer/VR content generator 118, an exemplary virtual reality user view 120, a heat lamp 122, a fan 124, and an aromatherapy diffuser 126.

In some embodiments, the headphones 116 are integrated into the virtual reality headset 114. In some embodiments, the headphones 116 are physically separate from the virtual reality headset 114. In some embodiments, the virtual reality augmented massage therapy system 100 includes a plurality of heat lamps comprising the heat lamp 122 and at least one other heat lamp. In some embodiments, the virtual reality augmented massage therapy system 100 includes a plurality of fans comprising the fan 124 and at least one other fan. In some embodiments, the virtual reality augmented massage therapy system 100 includes a plurality of aromatherapy diffusers comprising the aromatherapy diffuser 126 and at least one other aromatherapy diffuser.

To make the virtual reality augmented massage therapy system of the present disclosure, one would need a computer and VR headset running the specifically designed virtual reality software, which coincides with the set-up of the massage chair and sensory components. The virtual reality augmented massage therapy system also would need to be outfitted with an automated, electric massage chair and a virtual reality headset. The additional sensory components of the virtual reality augmented massage therapy system include an aromatherapy or fragrance diffuser, a heat lamp and electric fans positioned around the room. It is also possible to incorporate multiples of each or all of the sensory components in any implementation and deployment of a virtual reality augmented massage therapy system. Furthermore, the method, described in greater detail below by reference to FIG. 2, covers the usage of these separate devices to create a sense of immersion as the massage recipient is in a virtual reality headset. In addition, the virtual reality augmented massage therapy system can be synchronized and automated by the use of computer software which generates the virtual environment and also triggers the individual devices.

The virtual reality augmented massage therapy system can be further automated or improved by integrating some of the individual components into a single device or by combining certain elements which will in turn operate together. For example, the diffuser could be integrated as part of the fan system. The addition of external speakers and the use of sonic audio fields could also be used to further enhance the immersion, providing tactile feedback on the skin. Also, as virtual reality headsets advance in technology, some of the individual sensory devices may be directly integrated into the unit itself. For example, a future VR headset may offer a built-in fragrance diffuser. The virtual reality software will begin to usher the treatment recipient into a new environment using audio and visual means. Once the virtual reality program is underway, the sensory components are triggered and further submerge the treatment recipient into the immersive experience. In this way, the virtual reality augmented massage therapy system and the aforementioned components work together to heighten the immersion of the virtual reality environment and therefore enhance the massage experience for the user in a symbiotic way. Specifically, the use will experience a deep level of immersion and rest by using the listed equipment and following the general steps to be transported into a state of relaxation. Also, as a person of ordinary skill in the relevant art would appreciate, providing virtual reality augmented massage therapy via the virtual reality augmented massage therapy system can be adapted as technology improves and other technology or improved devices become available.

The method for providing virtual reality augmented massage therapy of the present disclosure generally works by following a series of steps for combining virtual reality environments with automated massage programs and external sensory components in order to help a person to believe they have been transported to a pleasurable, relaxing environment. For example, to trigger the immersive experience for this method, the following exemplary sequence may be carried out:

1. The treatment recipient gets seated in the automated massage chair first, before the virtual reality headset is applied. While it is possible to apply the virtual reality headset before the recipient sits in the automated massage chair, the preferred method intends to ensure that any necessary sensors and/or calibrations can be made while the seated person is stationary.

2. When the headset is put on, the computer or VR content generator starts the virtual reality software which provides the treatment recipient with a visual representation of the chair and their body in the virtual environment. This is an important step because it is the first indicator of 'presence' in the virtual environment and therefore the start of the immersion process. In addition, this "felt experience" or "felt sense" of surroundings may be enhanced by audible content through headphones, such as the headphones 116 integrated with the virtual reality headset 114, described above by reference to FIG. 1.

3. As the virtual environment is rendered, the corresponding sensory components are triggered to reflect elements within the virtual environment. In some embodiments, the sensory components are triggered to start along a particular order, with the first sensory component to be triggered being the aromatherapy diffuser, which emits fragrances that complement the virtual environment, followed by the second sensory component triggered being the ceramic heat lamp, which is positioned and calibrated to mimic the warmth of the sun in the virtual environment, and finally, the last sensory component being one or more fans being started, which are positioned and programmed to mimic the wind in the virtual environment. In some embodiments, the sensory components are triggered to start along a different order. In some other embodiments, the sensory components are triggered to start simultaneously.

4. When all of these steps are carried out, the treatment recipient can be physiologically ushered into a place of relaxation.

In some embodiments, the method for providing virtual reality augmented massage therapy includes a plurality of steps to engage multiple senses of a user to help the user evaluate their surroundings in order to relax and feel comfortable during massage therapy. In some embodiments, the plurality of steps of the method for providing virtual reality augmented massage therapy include (i) seating a user in an automated massage chair, (ii) placing a virtual reality headset onto the user to cover the user's eyes and ears, (iii) starting VR playback on the virtual reality headset by one of starting a virtual reality program on a virtual reality computing device that is communicably connected to the virtual reality headset and starting a VR content generator that is communicably connected to the virtual reality headset, (iv) initiating a massage program of a particular time duration by selection of a pre-programmed massage routine on the automated massage chair, (v) triggering a plurality of sensory devices comprising a fragrance diffuser, ceramic heat lamps, and fans, (vi) fading out the VR playback at the end of the particular time duration, and (vii) concluding the massage program by the automated massage chair.

Figure 2:
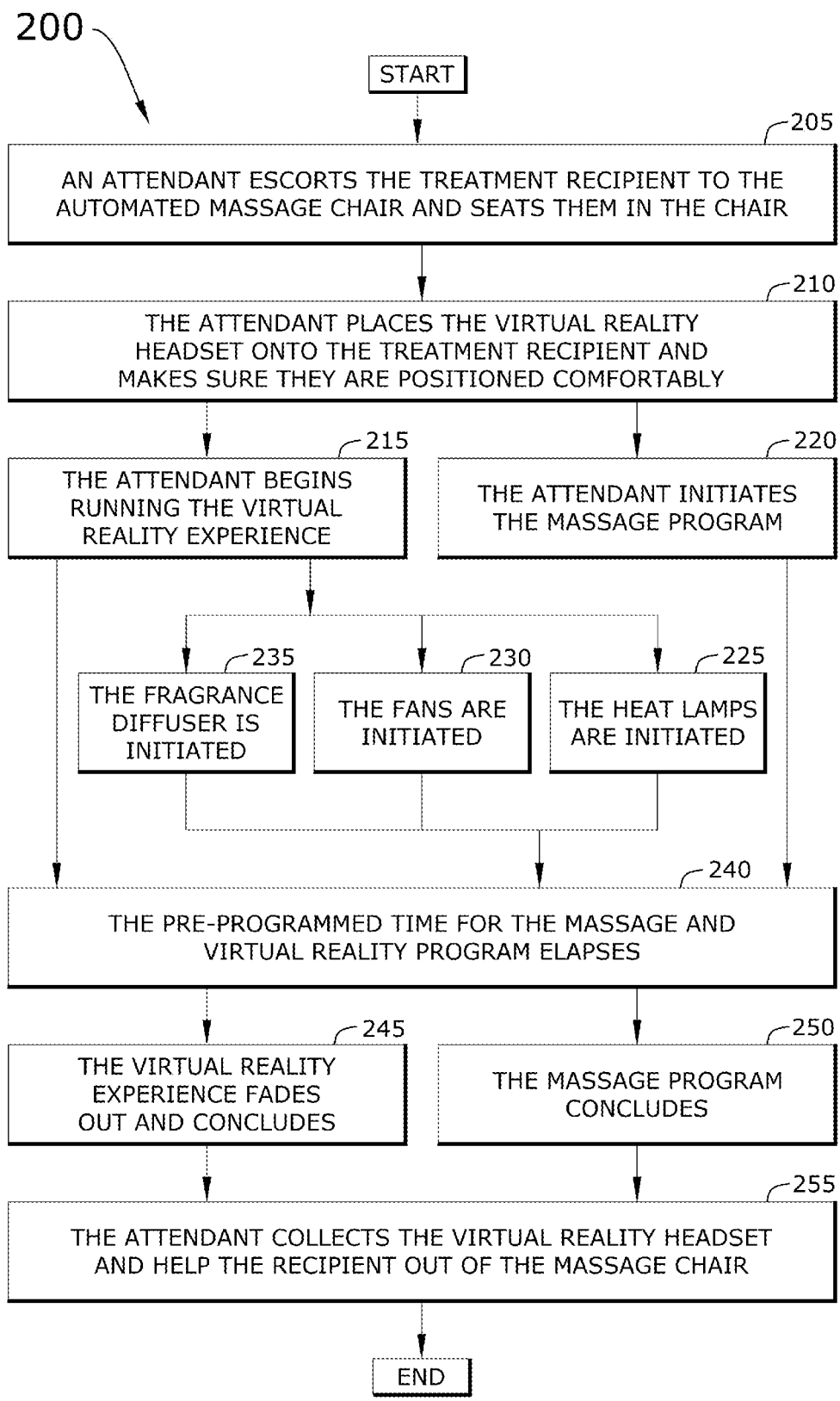
FIG. 2 conceptually illustrates a method for providing virtual reality augmented massage therapy in some embodiments.

By way of example, FIG. 2 conceptually illustrates a method for providing virtual reality augmented massage therapy 200. The following description of the method for providing virtual reality augmented massage therapy 200 is not intended to limit the scope or nature of the relationships between the various elements of the virtual reality augmented massage therapy system 100, but is intended as illustrative example only. As shown in this figure, the method for providing virtual reality augmented massage therapy 200 starts when an attendant escorts a virtual reality augmented massage treatment recipient (referred to in this example interchangeably as the "treatment recipient", the "massage recipient", or the "user") to the automated massage chair (at 205). The treatment recipient is seated in the automated massage chair during this step (at 205) of the method for providing virtual reality augmented massage therapy 200. The exemplary automated massage chair 112 described above by reference to FIG. 1 demonstrates the user 110 as seated.

In some embodiments of the method for providing virtual reality augmented massage therapy 200, after the user is seated in the automated massage chair, the attendant places the virtual reality headset onto the treatment recipient and makes sure the user is positioned comfortably in the automated massage chair (at 210). The exemplary automated massage chair 112 described above by reference to FIG. 1 demonstrates the user 110 as being comfortably settled. Furthermore, the virtual reality headset 114, described above by reference to FIG. 1, shows an example in which the headphones 116 are integrated into within the virtual reality headset 114.

In some embodiments of the method for providing virtual reality augmented massage therapy 200, after the treatment recipient is comfortably positioned in the automated massage chair, the attendant starts the virtual reality experience for the user (at 215). For example, the virtual reality experience may be visually output to the virtual reality headset with accompanied audio content the corresponds at some aural level to the visual show displayed in the headset. The virtual reality experience may be visually output by virtual reality software running on a computer or VR content generator, such as a VR content generation software program running on the computer/VR content generator 118 described above by reference to FIG. 1.

Contemporaneously with or immediately after starting the virtual reality experience, the attendant initiates the massage program (at 220). In some embodiments, the attendant initiates the massage program by selecting one of several pre-programmed, timed massage routines. In some embodiments, the attendant selects the massage program from a massage routine selection device that is connected physically or wirelessly to the automated massage chair. The attendant may also select a specific time, use a default time duration for the selected massage routine, or change the time of the selected massage routine. For example, the massage routine may allow the attendant to select a time duration of 20-60 minutes, inclusive. In some embodiments, the attendant initiates the massage program as near to the start of the virtual reality experience as possible. For example, as the virtual reality software begins its start-up process, the attendant may initiate the massage program, so that the virtual reality experience is largely co-incident with the massage program during the time duration for the program.

In some embodiments of the method for providing virtual reality augmented massage therapy 200, while the virtual reality experience and massage program get underway, the corresponding sensory devices are triggered. Specifically, the method for providing virtual reality augmented massage therapy 200 includes starting the heat lamp(s) (at 225), initiating the fan(s) (230), and initiating the fragrance diffuser(s) (at 235). In some embodiments, a heat lamp is a ceramic heat lamp. In some embodiments, the fragrance diffuser is an aromatherapy diffuser that emits a fragrance. In some embodiments, the corresponding sensory devices, including the heat lamp(s), the fan(s), and the fragrance diffuser(s), are triggered automatically by the virtual reality experience/program. In some embodiments, the corresponding sensory devices are simultaneously triggered by the virtual reality program. In some embodiments, the corresponding sensory devices are automatically triggered separately by the virtual reality program in order to start each sensory device at a particular time of the virtual reality experience/program. In some embodiments, the complete virtual reality experience is underway when the virtual reality program is running on the computing device and is both visually outputting the virtual reality experience on the virtual reality headset and audibly outputting the aural virtual reality soundtrack to the headphones, and when the massage chair is carrying out the programmed routine, the fragrance diffuser(s) is/are active, the heat lamp(s) is/are turned on, and the corresponding fan(s) is/are running.

In some embodiments, the the method for providing virtual reality augmented massage therapy 200 continues until the pre-programmed time period elapses for the massage program and virtual reality program (at 240). The pre-programmed time period, as noted above, can be set by the attendant from one of a default time for the massage program selected or a specific time selected and set by the attendant for the session (e.g., from 20 to 60 minutes). When the time period elapses, the method for providing virtual reality augmented massage therapy 200 of some embodiments proceeds to a step in which the virtual reality experience, provided through the virtual reality headset and headphones via the VR content generator or computer, fades out and concludes (at 245) and the massage program, provided by the automated massage chair, concludes (at 250). Specifically, the virtual reality augmented massage software will slowly fade out the virtual reality environment and conclude the session. In some embodiments of the method for providing virtual reality augmented massage therapy 200, the attendant collects the virtual reality headset and helps the treatment recipient out of the massage chair (at 255) which is at the conclusion of the session. Then the method for providing virtual reality augmented massage therapy 200 ends.

Additionally, the method of augmenting massage therapy with virtual reality and extra sensory components as described in this disclosure can be adapted for use in and applied to clinical treatment programs or physical therapy programs. Similarly, the system could also be adapted for use in and applied to beauty treatments which require long periods of sitting such as hair styling, pedicures, and manicures. The same system may also be adapted for use and applied to traditional massage therapy performed by a trained esthetician on a table or chair. This method could be altered to represent the 'virtual' table, chair or platform that any of these services are carried out on.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 3:
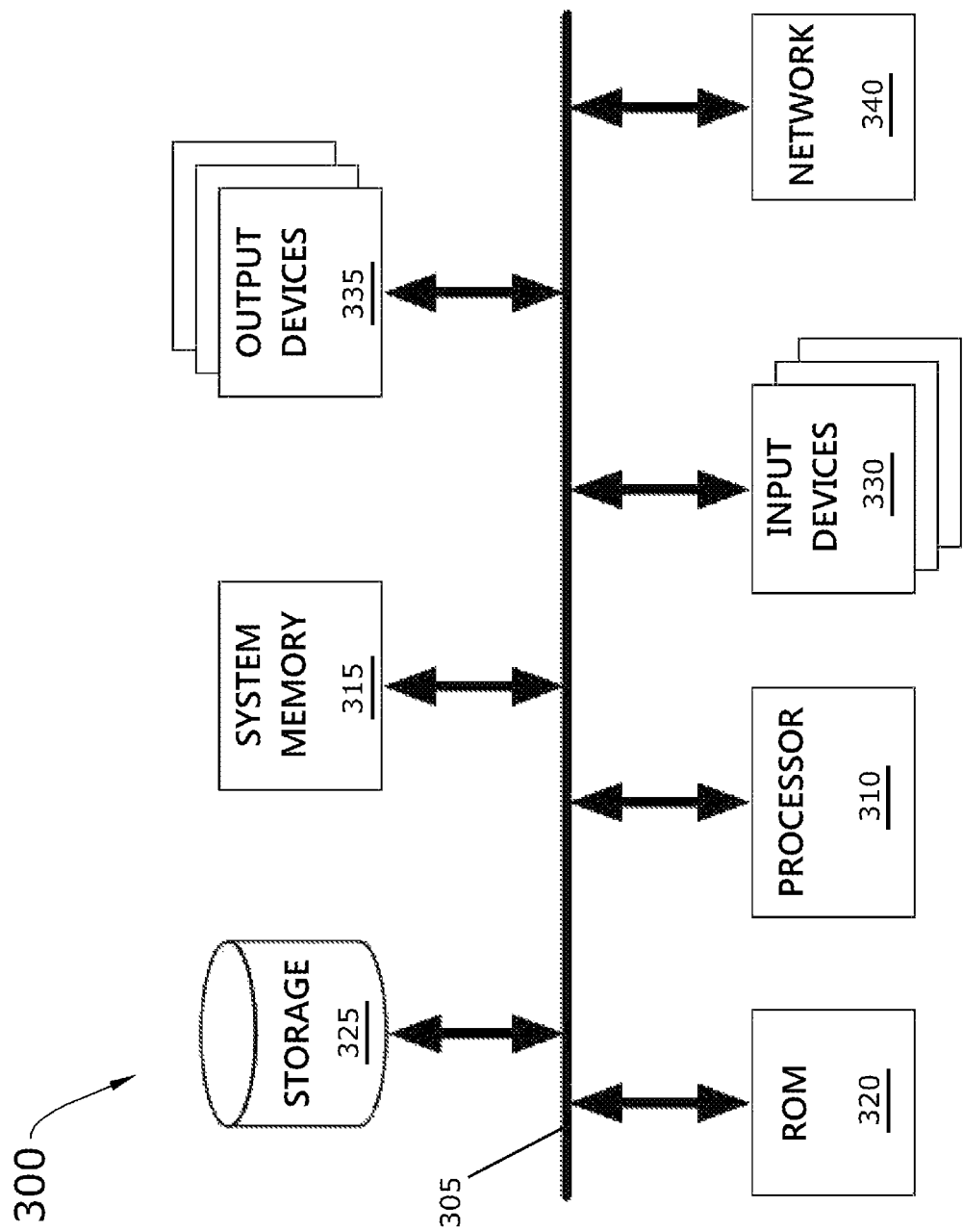
FIG. 3 conceptually illustrates an electronic system with which some embodiments of the invention are implemented.

FIG. 3 conceptually illustrates an electronic system 300 with which some embodiments of the invention are implemented. The electronic system 300 may be a computer, phone (cell phone, mobile phone, smartphone, etc.), PDA (iPod, other handheld computing device, etc.), or any other sort of electronic device or computing device. Such an electronic system includes various types of computer readable media and interfaces for various other types of computer readable media. Electronic system 300 includes a bus 305, processing unit(s) 310, a system memory 315, a read-only 320, a permanent storage device 325, input devices 330, output devices 335, and a network 340.

The bus 305 collectively represents all system, peripheral, and chipset buses that communicatively connect the numerous internal devices of the electronic system 300. For instance, the bus 305 communicatively connects the processing unit(s) 310 with the read-only 320, the system memory 315, and the permanent storage device 325.

From these various memory units, the processing unit(s) 310 retrieves instructions to execute and data to process in order to execute the processes of the invention. The processing unit(s) may be a single processor or a multi-core processor in different embodiments.

The read-only-memory (ROM) 320 stores static data and instructions that are needed by the processing unit(s) 310 and other modules of the electronic system. The permanent storage device 325, on the other hand, is a read-and-write memory device. This device is a non-volatile memory unit that stores instructions and data even when the electronic system 300 is off. Some embodiments of the invention use a mass-storage device (such as a magnetic or optical disk and its corresponding disk drive) as the permanent storage device 325.

Other embodiments use a removable storage device (such as a floppy disk or a flash drive) as the permanent storage device 325. Like the permanent storage device 325, the system memory 315 is a read-and-write memory device. However, unlike storage device 325, the system memory 315 is a volatile read-and-write memory, such as a random access memory. The system memory 315 stores some of the instructions and data that the processor needs at runtime. In some embodiments, the invention's processes are stored in the system memory 315, the permanent storage device 325, and/or the read-only 320. For example, the various memory units include instructions for processing appearance alterations of displayable characters in accordance with some embodiments. From these various memory units, the processing unit(s) 310 retrieves instructions to execute and data to process in order to execute the processes of some embodiments.

The bus 305 also connects to the input and output devices 330 and 335. The input devices enable the user to communicate information and select commands to the electronic system. The input devices 330 include alphanumeric keyboards and pointing devices (also called "cursor control devices"). The output devices 335 display images generated by the electronic system 300. The output devices 335 include printers and display devices, such as cathode ray tubes (CRT) or liquid crystal displays (LCD). Some embodiments include devices such as a touchscreen that functions as both input and output devices.

Finally, as shown in FIG. 3, bus 305 also couples electronic system 300 to a network 340 through a network adapter (not shown). In this manner, the computer can be a part of a network of computers (such as a local area network ("LAN"), a wide area network ("WAN"), or an intranet), or a network of networks (such as the Internet). Any or all components of electronic system 300 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 2 conceptually illustrates a process in which the specific operations of the process may not be performed in the exact order shown and described. Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

I claim:

1. A virtual reality augmented massage therapy system that taps into multiple human senses used by people to evaluate and make sense of their surroundings and thereby helping people to relax and feel comfortable, said virtual reality augmented massage therapy system comprising:

an automated massage chair comprising a plurality of selectable massage routines corresponding to a plurality of massage programs with a plurality of default time durations, wherein selection of any massage routine starts a timed massage session by the automated massage chair that is applied to a user seated in the automated massage chair;

a massage routine selection device that is communicably connected to the automated massage chair and configured to (i) receive selections of massage routines from the plurality of selectable massage routines, (ii) receive time duration data for each selected message routine, and (iii) trigger the automated massage chair to start a particular massage program corresponding to a particular massage routine as selected, wherein the time duration data comprises one of a default time duration and specific time duration that is different from the default time duration;

a virtual reality computing device comprising a processor, a memory, a persistent storage device, and a VR content generator program that is stored in the persistent storage device and runs on the processor when loaded into the memory, wherein the virtual reality computing device is a physical computing device that resides outside of and independently of the automated massage chair, wherein the VR content generator program is configured to (i) provide a virtual reality experience to the user seated in the automated chair approximately timed to coincide with the timed massage session and (ii) trigger one or more sensory devices in a plurality of sensory devices to create a heightened sense in the user of being immersed in the virtual reality experience during the timed massage session;

a virtual reality headset that is worn by the user when the user is seated in the automated massage chair, wherein the virtual reality headset is communicably connected to the virtual reality computing device and configured to visually output the virtual reality experience provided by the VR content generator program;

an aromatherapy diffuser sensory device of the plurality of sensory devices, wherein the aromatherapy diffuser sensory device is controlled by the VR content generator program running on the processor of the virtual reality computing device, wherein the VR content generator program automatically triggers the aromatherapy diffuser sensory device to start at a first time during the virtual reality experience as approximately timed to coincide with the timed massage session;

a ceramic heating lamp sensory device of the plurality of sensory devices, wherein the ceramic heating lamp sensory device is controlled by the VR content generator program running on the processor of the virtual reality computing device, wherein the VR content generator program automatically triggers the ceramic heating lamp sensory device to start at a second time during the virtual reality experience as approximately timed to coincide with the timed massage session; and a fan sensory device of the plurality of sensory devices, wherein the fan sensory device is controlled by the VR content generator program running on the processor of the virtual reality computing device, wherein the VR content generator program automatically triggers the fan sensory device to start at a third time during the virtual reality experience as approximately timed to coincide with the timed massage session.

2. The virtual reality augmented massage therapy system of claim 1, wherein the aromatherapy diffuser sensory device emits a fragrance.

3. The virtual reality augmented massage therapy system of claim 1, wherein the ceramic heating lamp sensory device provides heat that is applied to the user to simulate sun heat.

4. The virtual reality augmented massage therapy system of claim 1, wherein the fan sensory device blows air at the user seated in the automated massage chair to simulate wind.

5. The virtual reality augmented massage therapy system of claim 1, wherein the VR content generator program provides the virtual reality experience by starting and visually outputting a virtual reality content program that is visible to the user seated in the automated chair when the user is wearing the virtual reality headset, wherein the timed massage session approximately coincides with a starting point of the virtual reality content program when an attendant selects a specific massage routine through massage routine selection device as close in time to a time at which the virtual reality content program is started by the VR content generator program.

6. The virtual reality augmented massage therapy system of claim 5, wherein the virtual reality headset includes integrated audio headphones.

7. The virtual reality augmented massage therapy system of claim 6, wherein the VR content generator program further provides the virtual reality experience by audibly outputting an aural soundtrack program that is audible to the user seated in the automated chair when the user is wearing the virtual reality headset with the audio headphones.

8. The virtual reality augmented massage therapy system of claim 7, wherein the VR content generator program further provides the virtual reality experience for a particular duration of time that approximately coincides with the timed massage session applied by the automated massage chair to the user seated in the automated massage chair when the attendant selects to change the default time duration to the particular duration of time.

9. The virtual reality augmented massage therapy system of claim 8, wherein the first time, the second time, and the third time are specific ordered time instances within the particular duration of time at which the VR content generator program automatically triggers and sequentially starts each of the sensory devices including the aromatherapy diffuser sensory device, the heating lamp sensory device, and the fan sensory device.

10. The virtual reality augmented massage therapy system of claim 8, wherein the first time, the second time, and the third time are a same time instance within the particular duration of time at which VR content generator program automatically triggers and simultaneously starts all of the sensory devices including the aromatherapy diffuser sensory device, the ceramic heating lamp sensory device, and the fan sensory device.

* * * * *